United States Patent [19]
Walker et al.

[11] Patent Number: 5,616,299
[45] Date of Patent: Apr. 1, 1997

[54] DISPENSER FOR DRIED BIOLOGICAL REAGENT SPHERES

[75] Inventors: David W. Walker, Milwaukee; Brent A. Burdick, Brookfield; James F. Jolly, Glendale; Daniel D. Zender, Muskego, all of Wis.

[73] Assignee: Pharmacia Biotech, Inc., Milwaukee, Wis.

[21] Appl. No.: 469,050

[22] Filed: Jun. 6, 1995

[51] Int. Cl.$^6$ ............................ B01L 11/00; B65G 29/00
[52] U.S. Cl. ............................ 422/99; 221/197; 221/266; 221/277; 422/102
[58] Field of Search ...................... 422/99, 102; 221/266, 221/277, 197

[56] References Cited

U.S. PATENT DOCUMENTS

| | | | |
|---|---|---|---|
| 1,013,674 | 1/1912 | Millard . | |
| 1,120,500 | 12/1914 | Hughes . | |
| 1,269,768 | 6/1918 | Whitener . | |
| 1,980,859 | 6/1934 | Greve . | |
| 2,188,304 | 1/1940 | Surdenik | 312/84 |
| 2,256,340 | 5/1941 | Gora et al. . | |
| 2,669,349 | 2/1954 | Silver | 206/42 |
| 2,681,529 | 6/1954 | Braithwaite . | |
| 4,428,502 | 1/1984 | Veltri | 221/152 |
| 4,438,867 | 3/1984 | Mayne et al. | 221/197 |
| 4,474,308 | 10/1984 | Bergeron | 221/24 |
| 4,638,923 | 1/1987 | Mines et al. | 221/132 |
| 4,648,529 | 3/1987 | Blakemore et al. | 221/1 |
| 4,724,984 | 2/1988 | Wilken et al. | 221/266 |
| 4,896,792 | 1/1990 | Marchand | 221/11 |
| 4,929,428 | 5/1990 | Tezuka | 422/100 |
| 5,018,644 | 5/1991 | Hackmann et al. | 221/65 |
| 5,336,469 | 8/1994 | Tobiki et al. | 422/100 |
| 5,351,858 | 10/1944 | Bur-Yona et al. | 221/266 |
| 5,377,864 | 1/1995 | Blechl et al. | 221/2 |

FOREIGN PATENT DOCUMENTS

| | | |
|---|---|---|
| 0484244 | 5/1992 | European Pat. Off. . |
| 602568 | 9/1934 | Germany . |

*Primary Examiner*—Jill Warden
*Assistant Examiner*—Jan M. Ludlow
*Attorney, Agent, or Firm*—Quarles & Brady

[57] ABSTRACT

An apparatus for dispensing reagent spheres from a vial includes a housing with an inlet through which the reagent spheres are received from the vial. Within the housing is a dispensing tube which forms a passageway for the reagent spheres and which has a first relatively large section in communication with the inlet and a funnel section in which the passageway reduces in cross section to a narrower linearizing section. The cross sectional area of the linearizing section is only slightly larger than one of the reagent spheres being dispensed. A metering shaft extends across and blocks the linearizing section of the passageway. The metering shaft has a depression for conveying one reagent sphere at a time between portions of linearizing section when the metering shaft is rotated 180 degrees. A gear on the metering shaft meshes with teeth on a plunger which is slidably mounted to the housing. A user pressing the plunger causes the metering shaft to rotate transferring a reagent sphere to a portion of the passageway connected to the outlet of the housing and thereby ejects that reagent sphere from the housing.

20 Claims, 4 Drawing Sheets

DISPENSER FOR DRIED BIOLOGICAL REAGENT SPHERES

BACKGROUND OF THE INVENTION

The present invention relates to apparatus for dispensing biological materials and reagents; and more particularly to apparatus for dispensing glassy, porous reagent spheres into a laboratory vessel in which a reaction is to take place.

Few biologically active materials are sufficiently stable so that they can be isolated, purified, and then stored in solution at room temperature. As a consequence biological reagents often are provided in dried form to increase their storage stability. In preparing reagents for convenient and efficient testing of biological samples, it is frequently important to obtain dry chemical blends in uniform, discreet amounts. These reagents must be efficiently and economically prepared in small, precisely measured quantities for laboratory use.

One type of carrier which has been used to stabilize doses of biological reagents are glass-forming filler materials, such as a sucrose polymer. A measured amount of a biological reagent solution is incorporated into the filler material (which is a water-soluble or water-absorbing substance). The composite then is freeze dried to produce a reagent sphere having a composition which immobilizes and stabilizes the biological reagent. Examples of glass-forming filler materials for stabilizing biological reagents are described in F. Franks, "Long-Term Stabilization of Biologicals", 12 Bio-Technology 253 (1994); U.S. Pat. No. 5,098,893; U.S. Pat. No. 5,200,399; and U.S. Pat. No. 5,240,843.

The biological reagent spheres must be kept relatively dry during storage. Otherwise, moisture allows the filler material to change into a rubber state which causes the reagent contained therein to become unstable. As a consequence, reagent spheres must be stored in a container that prevents moisture from reaching them.

In order to use the reagent in a biological procedure or experiment, the carrier spheres have to be individually dispensed from the storage container. A dispenser for this purpose must have several characteristics. As noted previously, moisture adversely affects dried reagent spheres and thus the dispenser should be sealable to prevent moisture penetration between dispensing operations. Furthermore, the dried reagent spheres easily become charged with static electricity which causes them to cling to the walls of conventional dispensing apparatus. In addition, the dispensing apparatus has to individually meter out one reagent sphere at a time in a manner which does not crush the sphere. Because the diameter of the reagent spheres is not closely toleranced, the dispensing apparatus must be designed to accommodate spheres of varying diameter, if conventional spheres are to be accommodated.

It is also desirable to design the dispenser to avoid cross-contamination either due to use of a common dispenser with spheres containing different biological reagents or due to an outlet of the dispenser coming into contact with several laboratory vessels having different substances.

SUMMARY OF THE INVENTION

The general object of the present invention is to provide a dispenser for dried reagent spheres containing biological material.

Another object is to provide such a dispenser which can be held in and easily operated with one hand of a user to dispense individual reagent spheres directly into laboratory vessels.

A further object of the present invention is to provide a dispenser whose operation is unaffected by static electric charge on the reagent spheres.

Yet another object is to provide a dispenser which inhibits moisture in the ambient environment from being absorbed by the spheres stored for dispensing.

Still another object of the present invention is to provide a dispenser for biological reagent spheres which incorporates a mechanism which limits the usage of the container to designated types of reagents or biological material.

These and other objectives are fulfilled by an apparatus which includes a body formed of electrically conductive material. The body preferably comprises a housing with a tube that forms a passageway for the reagent spheres being dispensed. The housing has a size and shape that can be held easily in a user's hand and provides an inlet for receiving the reagent spheres from a vial. A metering shaft across the passageway dividing the passageway into two sections. A depression is provided in the metering shaft to convey one sphere at a time between the two sections of the passageway upon rotation of the metering shaft.

A plunger is slidably mounted in the body. A transmission couples the plunger to the metering shaft wherein sliding movement of the plunger produces rotation of the metering shaft. In the preferred embodiment, the transmission includes teeth on the plunger, and a gear connected to the metering shaft and meshing with the plunger teeth. A spring for biasing said plunger into a normal operating position.

In one embodiment of the dispenser the plunger extends through an aperture in the body and is directly operable by the user. In another embodiment, the plunger is enclosed in the body and is mechanically coupled to a coupling to which attaches the vial containing the reagent spheres. The coupling can slide within the body when the user presses on the vials. The sliding force is transferred to the plunger to produce rotation of the metering shaft and the dispensing of a reagent sphere.

DETAILED DESCRIPTION OF THE INVENTION

Figure 1:
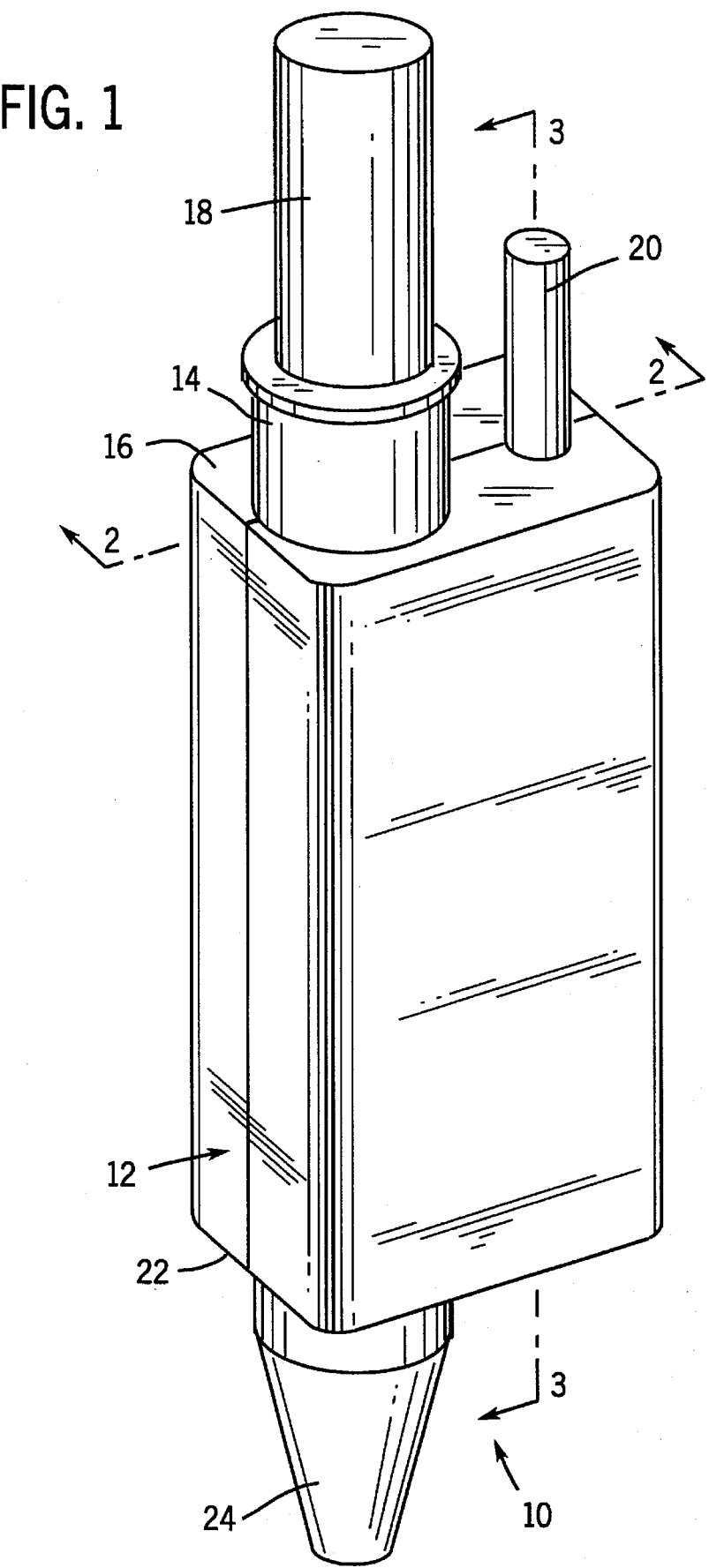
FIG. 1 is an isometric view of a dispenser according to the present invention.

With initial reference to FIG. 1, a dispenser 10 has a housing 12 forms a generally rectilinear body. A cylindrical coupling 14 projects from a first end 16 of housing 12 and has an opening in which to attach a vial 18 to the dispenser. The vial 18 is of the type commonly used by manufacturers to ship freeze-dried reagent spheres containing the biological reagent or other material to be dispensed. The first end 16 of the housing 12 also has a plunger 20 extending therefrom for activating the dispenser, as will be described. The opposite, or second, end 22 of housing 12 has an another opening with a conical shaped nozzle 24 attached thereto which forms a dispenser outlet through which the reagent spheres are ejected.

Figure 2:
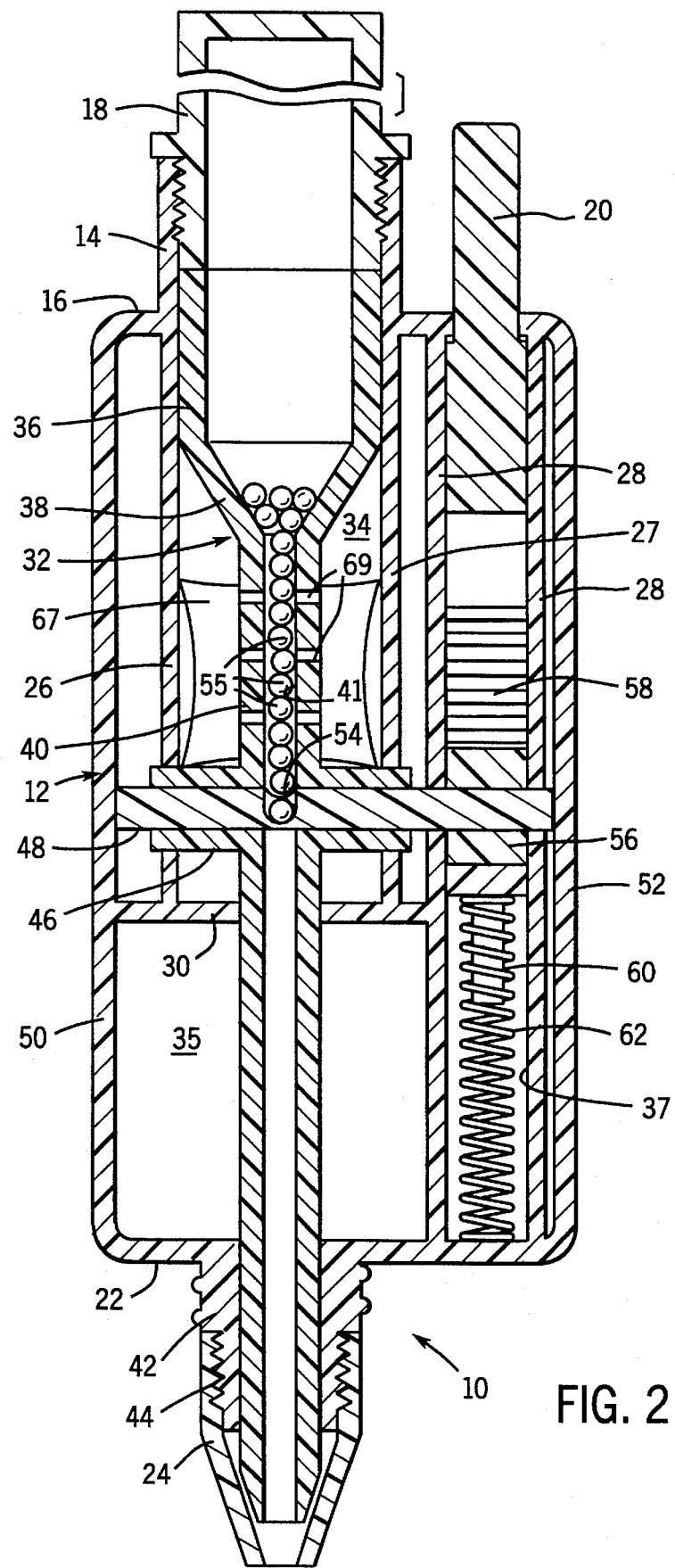
FIG. 2 is a cross section view taken along line 2—2 of the FIG. 1.

Referring to FIG. 2, the housing 12 has a hollow interior which is subdivided by a plurality of walls 26, 27, 28 and 30 into a number of internal chambers 34, 35 and 37. A dispensing tube 32 has an upper section located within one such chamber 34 between walls 26 and 27. The dispensing tube 32 has a wide mouth section 36 which opens into the interior of the cylindrical coupling 14. The opposite end of wide mouth section 36 is connected by a tapering or funnel-like section 38 to a narrower linearizing section 40 of the dispensing tube 32. Linearizing section 40 continues through the housing 12, exiting through an aperture in the other end 22. Upon exiting, the linearizing section 40 of the dispensing tube 32 passes through a column 42 having a reduced diameter portion with external screw threads 44 that engage internal screw threads on the nozzle 24. The nozzle is disposable and may be replaced after dispensing reagent spheres for a given laboratory procedure to prevent cross contamination between different experiments.

The dispensing tube 32 has a cross tube 46 extending transversely across the linearizing section 40 between the interior housing walls 26 and 27. A metering shaft 48 extends through the cross tube 46 between exterior side walls 50 and 52 of the dispenser 10. The metering shaft 48 has a depression 54 therein which is aligned with the inner passageway 41 through the linearizing section 40 of the dispensing tube 32. The diameter and depth of the depression 54 is sufficient to receive only one of the reagent spheres contained within the dispensing tube 32. As will be described, rotation of the metering shaft 48 carries the received reagent sphere between upper and lower portions of the linearizing section 40, as will be described. One end of the metering shaft 48 protrudes into the housing chamber 37 formed between interior walls 28 and 29. A gear 56 is securely attached to the metering shaft between walls 28 and 29 and engages teeth 58 on the surface of plunger 20. The interior end of the plunger 20 has a rod 60 projecting therefrom into a compression spring 62 that extends between the plunger 20 and the interior surface at the second end 22 of the housing 12.

As noted previously, the freeze-dried reagent spheres become charged with static electricity. Therefore, to prevent those spheres from clinging to the walls of the dispenser 10 due to that charge, components of the dispenser which come into contact with the reagent spheres and the housing 12 are made of an electrically conductive material to dissipate the static electrical charge. For example, those components can be formed of a carbon filled plastic, such as a polycarbonate, although a metal filled plastic or metal housing also could be employed.

Figure 4:
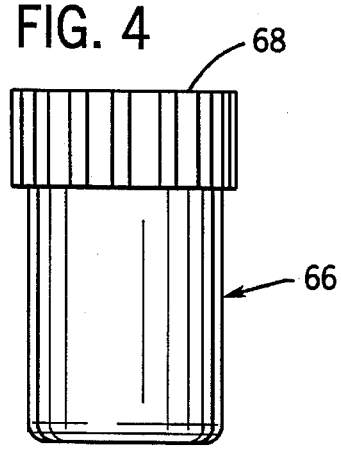
FIG. 4 illustrates a cap which is used to seal an outlet of the dispenser.

A cap 66, shown in FIG. 4 has an open end 68 with internal screw threads adapted to engage the external screw threads on the column 42 which extends from the nozzle end 22 of housing 12. The cap is sufficiently deep so as to enclose the nozzle 24 when inserted on the column 42 and close that end opening of housing 12. For example, cap 66 may seal the vial 18 during shipment from the manufacturer of the reagent spheres and then used to cover the nozzle 24 after the vial is attached to the dispenser 10. Placing the cap 66 on the housing 12 also retains the cap for use in resealing the vial 18 upon subsequent removal from the dispenser 10. Normally the engagement of vial 18 with the coupling 14 closes the opening at the other end of the housing 12 so that moisture can not enter the dispenser when not in use.

To further inhibit moisture from being absorbed by the reagent spheres, conventional desiccant material is placed inside the dispenser 10, as shown in FIG. 2. Preferably, desiccant material 67 contained in an envelope of porous paper is placed in housing chamber 34 adjacent to the dispenser tube 32. A plurality of small holes 69 extend through the linearizing section 40 of the dispensing tube so that the desiccant can absorb moisture from inside the tube. Alternatively the desiccant material 67 can be placed in other chambers in the housing 12, such as lower chamber 35 in which case the dispensing tube holes 69 would be located in the portion of the linearizing section 40 in that chamber.

In order to use the present dispenser 10, the housing 12 is inverted so that the first end 16 is facing downward. A cap 66 on the vial 18 containing the freeze-dried reagent spheres is removed and screwed into the opening on the end of the dispenser coupling 14. The internal screw threads on the dispenser coupling 14 match the pitch of the screw threads on the vial 18. Different biological reagents can be distributed in vials having differing diameters and thread pitches with similarly configured openings in the dispenser coupling 14. Thus, a specific dispenser can be designed for use with a specific biological reagent and cannot be used with other biological materials shipped in different sized vials.

The dispenser housing 12 then is inverted which causes the reagent spheres 55 within the vial 18 to fall downward into the dispensing tube 32 as shown in FIG. 2. The spheres 55 are funneled by the tapering section 38 of the dispensing tube 32 into the narrower linearizing section 40. As previously note, the passageway 41 through the tubular portion is slightly greater than the largest diameter of a reagent sphere that is to be dispensed. Thus, only one sphere at a time can pass from the tapering section 38 into the passageway 41 and the spheres 55 become stacked therein. The force exerted by spring 62 pushes the plunger 20 into the upward position shown in the drawings. In that position, the teeth 58 on plunger 20 rotate the gear 56 and metering shaft 48 into a position at which the depression 54 is facing vial 18. This allows one of the reagent spheres 55 to drop into the depression 54 as illustrated.

The user then positions the nozzle 24 over a test tube or other laboratory vessel into which a freeze-dried reagent sphere is to be dispensed. The plunger 20 is pressed into the housing 12 which action causes the teeth 58 to rotate the gear 56 and metering shaft 48 within the housing. The reagent sphere that nests inside depression 54 moves with the metering shaft 48 within the passageway 41 through the dispensing tube 32. The length of travel of plunger 20 within the housing 12 is limited by tab 61 on the plunger striking an internal housing wall 63 shown in FIG. 3. The length of plunger travel and the number of teeth 58 are such that movement of the plunger 20 between extreme outward and inward positions causes a 180 degree rotation of the metering shaft 48 between positions at which depression 54 opens upward and downward in the orientation of a device shown in the drawings. The rotation of the metering shaft 48 and its curved outer wall gently pushes upward the second lowest reagent sphere within the dispensing tube passageway 41. These physical characteristics of the metering shaft 48 prevent the second lowest reagent sphere from being sheared or crushed during the dispensing operation.

The downward facing position of aperture 54 at the extreme inward depression of the plunger 20 causes the reagent sphere within the depression to drop downward, continuing through the interior passageway 41 of the dispensing tube 32 and falling out of the dispenser through the nozzle 24. Because the depression 54 is sized to accommodate only a single reagent sphere at a time, each operation of the plunger 20 permits only a single sphere to be ejected through the nozzle 24.

Once a reagent sphere has been ejected, the user releases the plunger 20 which returns to the extended position due to the force of spring 62. If the dispenser 10 is continued to be held upright as illustrated, another reagent sphere within the dispensing tube passageway 41 drops into the depression 54 when the metering shaft 48 returns to its normal position.

When the use of the dispenser 10 is complete, the cap 66 then may be placed over the nozzle 24 sealing that opening of the dispenser. Alternatively, the user may invert the dispenser thereby causing the freeze-dried reagent spheres 55 within the dispensing tube 32 to fall into the vial 18 which then can be unscrewed from the dispenser coupling 14 and sealed with cap 66.

Figure 5:
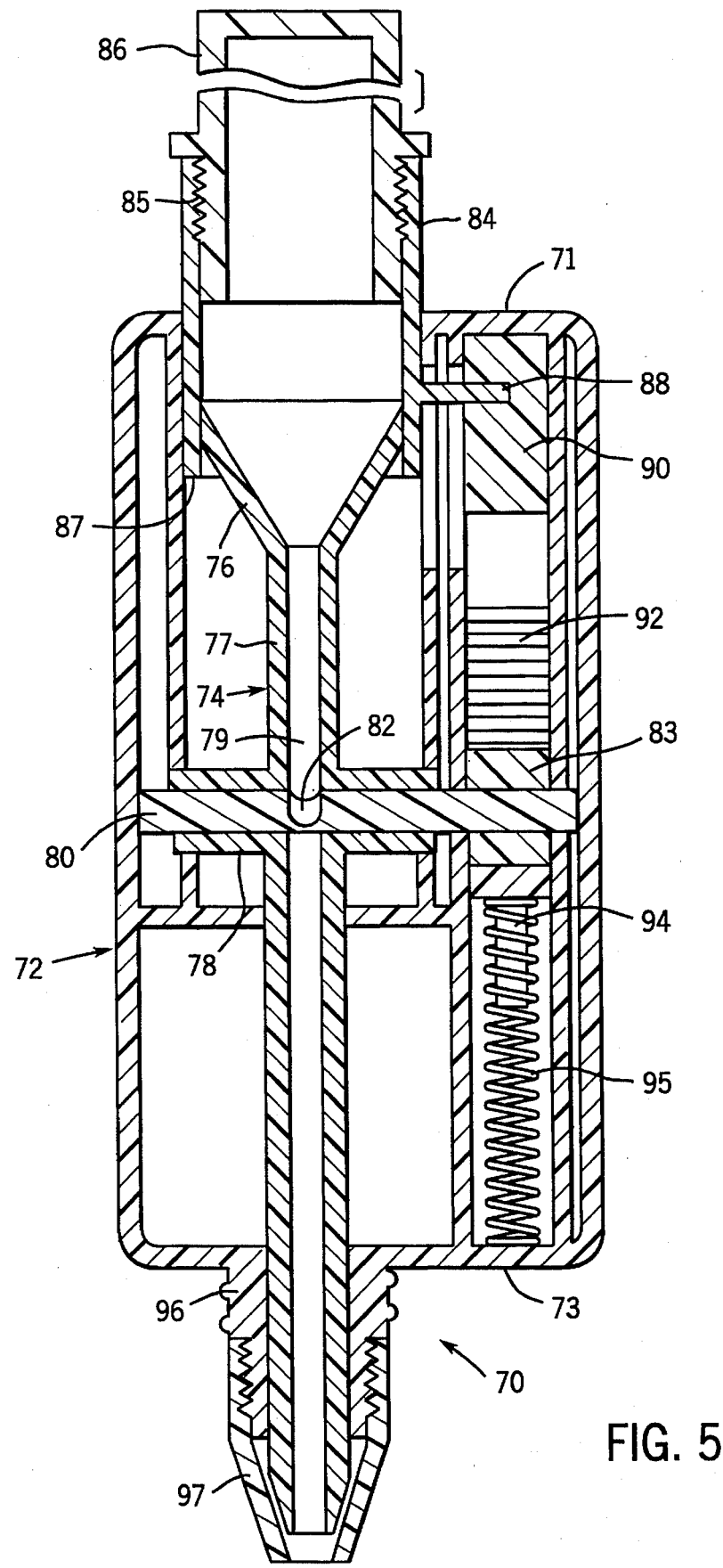
FIG. 5 is a cross section view, similar to that of FIG. 2, of another embodiment of the present invention.

FIG. 5 illustrates a second dispenser 70 according to the present invention. Dispenser 70 includes a housing 72 within which is positioned a dispensing tube 74 having a funnel section 76 which opens into a narrower linearizing section 77. The linearizing section 77 of dispensing tube 74 extends through an opening in a collar 96 in the second end 73 of housing 72. A disposable nozzle 97 is screwed onto the collar 96. Linearizing section 77 has a cross tube 78 extending transversely there across with a through passage that communicates with the central passageway 79 through the linearizing section 77. A metering shaft 80 extends through the cross tube 78 and has a depression 82 aligned with the central passageway 79. The depression 82 is sized to receive one reagent sphere to be dispensed. A gear 83 is secured to metering shaft 80.

A first end 71 of the dispenser housing 72 has an opening through which an actuator tube 84 slideably projects. The exterior end of the actuator tube 84 has internal screw threads 85 which mate with the screw threads on a vial 86 containing the reagent spheres to be dispensed. The interior end 87 of the actuator tube 84 extends around a mouth of the funnel section 76 of dispenser tube 74. The funnel section rides against the inside diameter of the actuator tube 84 so that the reagent spheres cannot pass therebetween. A peg 88 extends from one side of the actuator tube 84 into an aperture in a plunger 90. Unlike the plunger 20 in the first embodiment of dispenser 10, plunger 90 does not extend out of the dispenser housing 72. The plunger 90 has a set of gear teeth 92 which engage the teeth on gear 83. A shaft 94 extends from the lower end of the plunger 90 and is received within a compression spring 95.

Figure 3:
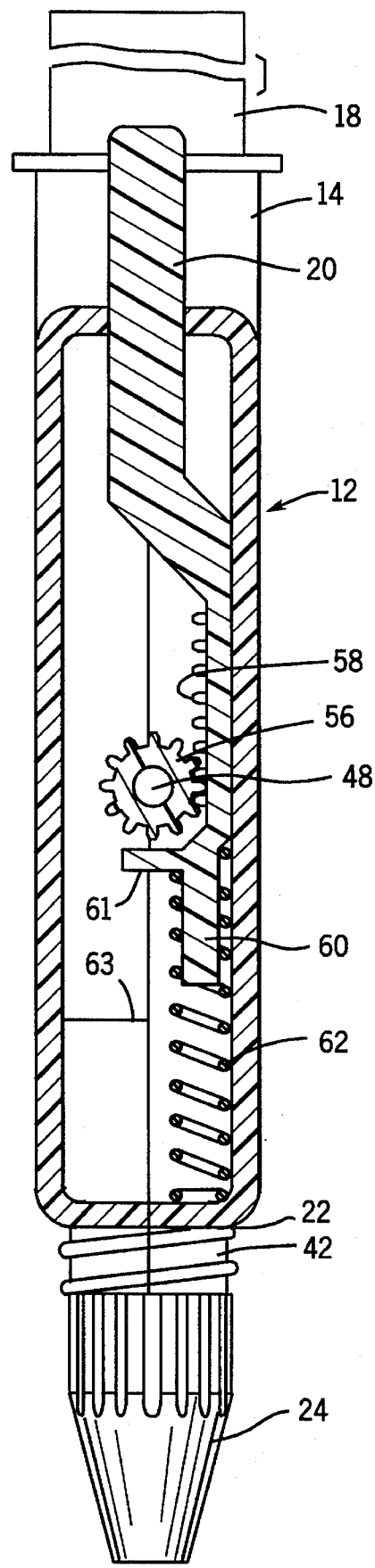
FIG. 3 is a cross section view taken along line 3—3 of FIG. 1.

The second dispenser 70 is used in much the same way as was described with respect to dispenser 10 in FIGS. 1–3. However, in order to dispense a reagent sphere, the user presses the closed end of the vial 86 into the dispenser housing 72 which also causes the actuator tube 84 to slide inward. As actuator tube 84 moves, force is transferred by pin 88 to plunger 90 which travels downward in the orientation of the dispenser 70 in FIG. 5. This downward movement and engagement of plunger teeth 92 with the teeth of gear 83 cause rotation of the gear and the metering shaft 80 connected thereto. The rotation of the metering shaft 80 conveys a reagent sphere between upper and lower portions of the dispensing tube 74. At the extreme inward position of the actuator tube 84, the metering shaft depression 82 has moved into alignment with the lower portion of the linearizing section 77 of dispensing tube 74 and the reagent sphere drops through the tube and nozzle 97. When the user releases the force on the vial 84, spring 97 causes the plunger, actuator tube 84 and the vial 86 to move upward to its normal position as illustrated. As this movement occurs, the gear 83 and metering shaft 80 are rotated into their normal position in which the depression 82 is oriented upward to receive another reagent sphere.

We claim:

1. An apparatus for dispensing reagent spheres from a vial, said apparatus comprising:
   a body formed of electrically conductive material having an inlet to which the vial can be coupled, an outlet and a passageway extending from the inlet to the outlet;
   a metering shaft across the passageway to divide the passageway into two portions and having a depression for conveying one reagent sphere at a time between the two portions of the passageway upon rotation of said metering shaft;
   a plunger slidably mounted on said body; and
   a transmission coupling said plunger to said metering shaft wherein sliding movement of the plunger within said body causes rotation of said metering shaft.

2. The apparatus as recited in claim 1 wherein said plunger has teeth thereon; and said transmission comprises a gear attached to said metering shaft and having teeth which mesh with the teeth on said plunger.

3. The apparatus as recited in claim 1 wherein said body is formed of an electrically conductive plastic.

4. The apparatus as recited in claim 1 further comprising a desiccant within said body.

5. The apparatus as recited in claim 1 further comprising a spring which biases said plunger with respect to said body.

6. The apparatus as recited in claim 1 wherein the inlet of said body has threads of a given pattern for engaging threads of a matching pattern on the vial, whereby the given pattern of threads restricts use of the apparatus to vials containing certain types of reagent spheres.

7. The apparatus as recited in claim 1 wherein said body comprises:
   a housing having a first opening which forms the inlet through which reagent spheres are received from the vial and a second opening which forms the outlet through which reagent spheres are dispensed from the apparatus; and
   a dispensing tube within said housing and forming the passageway between the first and second openings, and having a first section with an opening in communication with the first opening of said housing and a second section in which the passageway has a smaller cross section area than in the first section, the second section including an aperture through which said metering shaft extends.

8. The apparatus as recited in claim 7 wherein said dispensing tube further comprises a cross tube transverse to the second section and having a passage through the cross tube which communicates with the passageway; and wherein said metering shaft extends into the cross tube.

9. The apparatus as recited in claim 7 further comprising a nozzle attached at the second opening to said housing.

10. The apparatus as recited in claim 9 wherein the second section of said dispensing tube projects from said housing into said nozzle.

11. The apparatus as recited in claim 9 wherein said plunger has an end which protrudes from said body for operation by a user of the apparatus.

12. The apparatus as recited in claim 1 wherein said body comprises:
   a housing having a first opening which forms the inlet and a second opening which forms the outlet through which reagent spheres are dispensed from the apparatus;
   a tubular collar for coupling the vial to the apparatus and being slidably located in the first opening of said housing, said collar being mechanically tied to said plunger so as to move together with respect to said housing; and a dispensing tube forming the passageway, and having a first section with an opening through which enter reagent spheres which have passed through the tubular collar and having a second section wherein the passageway has a smaller cross section area than in the first section, the second section including an aperture through which said metering shaft extends.

13. An apparatus for dispensing biological reagent spheres from a vial, said apparatus comprising:

a housing having a first opening through which reagent spheres are received from the vial and a second opening through which reagent spheres are dispensed from the apparatus; and a dispensing tube forming a passageway for a reagent sphere to pass through the apparatus, and having a first section with an opening in communication with the first opening of said housing, a second section wherein the passageway has a smaller cross section area than in the first section, the second section including an aperture through which said metering shaft extends, and a cross tube extending transversely across and connected to the second section, and having a passage through the cross tube and in communication with the passageway;

a metering shaft extending into the cross tube and having a depression for conveying one reagent sphere at a time between sections of the passageway on opposite sides of the cross tube, such conveying occurring upon rotation of said metering shaft;

a gear attached to said metering shaft and having teeth;

a plunger slidably mounted within and projecting from said housing and having a plurality of teeth meshed with the teeth of said gear wherein sliding of said plunger within the housing rotates said gear and said metering shaft; and a spring which biases said plunger.

14. The apparatus as recited in claim 13 further comprising a desiccant within said housing.

15. The apparatus as recited in claim 13 further comprising a nozzle removably attached at the second opening to said housing.

16. The apparatus as recited in claim 15 wherein the second section of said dispensing tube projects outward from said housing into said nozzle.

17. An apparatus for dispensing reagent spheres from a vial, said apparatus comprising:

a housing having a first opening through which reagent spheres are received from the vial and a second opening through which reagent spheres are dispensed from the apparatus; and a collar for coupling the vial to the apparatus and slideably positioned within the first opening;

a dispensing tube forming a passageway for a reagent sphere to pass through the apparatus, and having a first section with an opening in communication with the first opening of said housing, a second section wherein the passageway has a smaller cross section area than in the first section, the second section including an aperture through which said metering shaft extends, and a cross tube extending transversely across and connected to the second section, and having a passage through the cross tube and in communication with the passageway;

a metering shaft extending into the cross tube and having a depression for conveying one reagent sphere at a time between sections of the passageway on opposite sides of the cross tube, such conveying occurring upon rotation of said metering shaft;

a gear attached to said metering shaft and having teeth;

a plunger slidably mounted in said housing and mechanically connected to said collar, said plunger having a plurality of teeth meshed with the teeth of said gear; and a spring which biases said plunger.

18. The apparatus as recited in claim 17 further comprising a desiccant within said housing.

19. The apparatus as recited in claim 17 further comprising a nozzle removably attached at the second opening to said housing.

20. The apparatus as recited in claim 19 wherein the second section of said dispensing tube projects outward from said housing into said nozzle.

* * * * *